United States Patent
Lange

(10) Patent No.: US 11,253,552 B2
(45) Date of Patent: Feb. 22, 2022

(54) PROCESS FOR PRODUCING EGG YOLK WITH HIGH CONTENT OF AF-16

(71) Applicant: LANTMÄNNEN AS-FAKTOR AB, Stockholm (SE)

(72) Inventor: Stefan Lange, Gothenburg (SE)

(73) Assignee: LANTMÄNNEN AS-FAKTOR AB, Stockholm (SE)

( * ) Notice: Subject to any disclaimer, the term of this patent is extended or adjusted under 35 U.S.C. 154(b) by 0 days.

(21) Appl. No.: 15/741,627

(22) PCT Filed: Jun. 20, 2016

(86) PCT No.: PCT/EP2016/064114
§ 371 (c)(1),
(2) Date: Jan. 3, 2018

(87) PCT Pub. No.: WO2017/009004
PCT Pub. Date: Jan. 19, 2017

(65) Prior Publication Data
US 2019/0231825 A1   Aug. 1, 2019

(30) Foreign Application Priority Data

Jul. 10, 2015 (SE) .................................. 1551018-3

(51) Int. Cl.
| | | |
|---|---|---|
| *A61K 35/57* | (2015.01) | |
| *A23K 50/75* | (2016.01) | |
| *A23L 15/00* | (2016.01) | |
| *A23K 10/30* | (2016.01) | |
| *A23K 20/142* | (2016.01) | |
| *A23K 20/163* | (2016.01) | |
| *A23K 20/10* | (2016.01) | |
| *A23L 33/17* | (2016.01) | |
| *A61P 1/08* | (2006.01) | |
| *A61K 38/10* | (2006.01) | |

(52) U.S. Cl.
CPC .............. *A61K 35/57* (2013.01); *A23K 10/30* (2016.05); *A23K 20/10* (2016.05); *A23K 20/142* (2016.05); *A23K 20/163* (2016.05); *A23K 50/75* (2016.05); *A23L 15/00* (2016.08); *A23L 15/20* (2016.08); *A23L 33/17* (2016.08); *A61K 38/10* (2013.01); *A61P 1/08* (2018.01); *A23V 2002/00* (2013.01)

(58) Field of Classification Search
None
See application file for complete search history.

(56) References Cited

U.S. PATENT DOCUMENTS

| | | |
|---|---|---|
| 5,296,243 A | 3/1994 | Lange et al. |
| 6,863,903 B2 | 3/2005 | Lange et al. |

FOREIGN PATENT DOCUMENTS

| | | |
|---|---|---|
| EP | 2363140 A1 | 9/2011 |
| EP | 1734989 B1 | 3/2012 |
| JP | 02-211831 A | 8/1990 |
| JP | 02-211832 A | 8/1990 |
| KR | 10-0165692 B1 | 12/1998 |
| KR | 10-0635179 B1 | 10/2006 |
| WO | WO91/09536 A1 | 7/1991 |
| WO | WO00/38535 A1 | 7/2000 |
| WO | WO02/063948 A2 | 8/2002 |
| WO | WO2014/096384 A1 | 6/2014 |

OTHER PUBLICATIONS

Hannsson et al. (2012) Acta neurochir Suppl. vol. 114: 377-382. (Year: 2012).*
Jennische et al. (2009) Old Herborn Univ. Semin. Monogr. vol. 22: 93-103 (Year: 2009).*
Lang et al. (1994) British Poultry Science 35: 615-620. (Year: 1994).*
Alam et al. (2011) J. Health Popul. Nutr. (4): 297-302. (Year: 2011).*
Kaya et al. (2017) Clin. Nutr. Experimental 12: 27-36. (Year: 2017).*
Website document entitled: "Salovum(R)" (available at www.poapharma.com/en/head_neck_salovum/). Downloaded from website Dec. 30, 2019. (Year: 2007).*
Zaman et al. (2014) Acta Paediatrica 103: 659-664. (Year: 2014).*
Cardoso, A. S., et al., "Nutritional requirement of digestible tryptophan for white-egg layers of 60 to 76 weeks of age," J. Appl. Poult. Res. 2014;23:729-734.

(Continued)

*Primary Examiner* — Russell G Fiebig
(74) *Attorney, Agent, or Firm* — Cermak Nakajima & McGowan LLP; Malcolm K. McGowan

(57) ABSTRACT

The present invention relates to a process for producing an egg yolk with a very high content of antisecretory factor (AF) proteins, in particular with a very high content of AF protein fragment consisting essentially of the amino acid sequence as shown in SEQ.ID.NO.1 (AF-16) and/or in SEQ.ID.NO.2 (AF-8), said process comprising for at least 4 weeks feeding a poultry, such as a hen, an AF-16 inducing pelleted feed for poultry comprising at least 0.14% free tryptophan, such as 1-2 g tryptophan/kg feed, and thereafter harvesting egg from said poultry, separating egg yolk from egg white, and alternatively spray-drying, grinding, leaching, extracting, evaporating, membrane filtrating, and/or or freeze-drying said egg yolk.

The present invention further relates to said egg yolk with a very high content of antisecretory factor (AF) proteins, produced according to the herein described process, and to their use for the preparation of functional food products and pharmaceutical products for the treatment and prophylaxis of abnormal physiological conditions caused e.g. by exceptionally high levels of body fluid discharge. The invention also relates to food products and pharmaceutical products so prepared.

18 Claims, 3 Drawing Sheets

Specification includes a Sequence Listing.

(56) References Cited

OTHER PUBLICATIONS

Lange, S., et al., "Concentrations of Antisecretory Factor in Eggs and in Chicken Blood Plasma," Br. Poultry Sci. 1994;35:615-620.
Zaman, S., et al., "Antisecretory factor effectively and safely stops childhood diarrhoea: a placebo-controlled, randomised study," Acta Paediatrica 2014;103(6):659-664.
International Search Report and Written Opinion for PCT Patent App. No. PCT/EP2016/064114 (dated Aug. 17, 2016).
Communication Purusant To Article 94(3) EPC from European Patent App. No. 16729926.2 (dated May 21, 2019).
Corzo, A., et al., "Dietary tryptophan effects on growth and stress responses of male broiler chicks," British Poultr Science 2005;46(4):478-484.
Further Examination Report from New Zealand Patent App. No. 738561 (dated Apr. 2, 2019).
National Research Council, "Nutrient Requirements of Poultry: Ninth Revised Edition, 1994" Mar. 1, 1994, Washington, DC, The National Academies Press, pp. 19-34.
Mozdeh Emadi et al., Dietary Tryptophan Effects on Growth Performance and Blood Parameters in Broiler Chicks, Journal of Animal and Veterinary Advances, Apr. 2010, pp. 700-704, vol. 9(4).
Robert Blair et al., Growth Responses of Broiler Chicks to Different Levels of Threonine and Tryptophan in Chemically-Defined Diets, Journal of Poultry Science, 2007, pp. 305-313, vol. 44.
Communication Pursuant To Article 94(3) EPC for European Patent App. No. 16729926.2 (dated Apr. 16, 2020).
Lange, S., "Antisekretorisk faktor motverkar inflammation och sekretion hos den sjuka patienten," Fou I Sverige 2014, revised 2018, Project No. 160331, https://www.researchweb.org/is/sverige/project/160331, downloaded Apr. 3, 2020, pp. 1-12, with English language translation thereof.
Yongkang, P., et al., "Modern Drying Technology," Chemical Industry Press, May 31, 2007, pp. 1-3.
Office Action from Chinese Patent App. No. 201680040903.X (dated Jul. 5, 2021) with English language translation thereof.

* cited by examiner

SEQUENCE LISTING

```
<160> NUMBER OF SEQ ID NOS: 4

<210> SEQ ID NO 1
<211> LENGTH: 16
<212> TYPE: PRT
<213> ORGANISM: artificial sequence
<220> FEATURE:
<223> OTHER INFORMATION: amino acids 36-51 of full-length human AF
      protein
<220> FEATURE:
<221> NAME/KEY: VARIANT
<222> LOCATION: 6
<223> OTHER INFORMATION: may be replaced with A
<221> NAME/KEY: VARIANT
<222> LOCATION: 3
<223> OTHER INFORMATION: may be replaced with R or K
<221> NAME/KEY: VARIANT
<222> LOCATION: 4
<223> OTHER INFORMATION: may be replaced with L
<221> NAME/KEY: VARIANT
<222> LOCATION: 2
<223> OTHER INFORMATION: may be replaced by S

<400> SEQUENCE: 1

Val Cys His Ser Lys Thr Arg Ser Asn Pro Glu Asn Asn Val Gly Leu
1               5                   10                  15

<210> SEQ ID NO 2
```

-continued

```
<211> LENGTH: 7
<212> TYPE: PRT
<213> ORGANISM: Artificial sequence
<220> FEATURE:
<223> OTHER INFORMATION: amino acids 37-42 of full-length human AF
      protein
<220> FEATURE:
<221> NAME/KEY: VARIANT
<222> LOCATION: 6
<223> OTHER INFORMATION: may be replaced by A
<221> NAME/KEY: VARIANT
<222> LOCATION: 3
<223> OTHER INFORMATION: may be replaced by R or K
<221> NAME/KEY: VARIANT
<222> LOCATION: 4
<223> OTHER INFORMATION: may be replaced by L
<221> NAME/KEY: VARIANT
<222> LOCATION: 2
<223> OTHER INFORMATION: may be replaced by S

<400> SEQUENCE: 2

Val Cys His Ser Lys Thr Arg
1               5

<210> SEQ ID NO 3
<211> LENGTH: 6
<212> TYPE: PRT
<213> ORGANISM: Artificial sequence
<220> FEATURE:
<223> OTHER INFORMATION: amino acids 38-42 of full-length human AF
      protein
<220> FEATURE:
<221> NAME/KEY: VARIANT
<222> LOCATION: 5
<223> OTHER INFORMATION: may be replaced by A
<221> NAME/KEY: VARIANT
<222> LOCATION: 2
<223> OTHER INFORMATION: may be replaced by R or K
<221> NAME/KEY: VARIANT
<222> LOCATION: 3
<223> OTHER INFORMATION: may be replaced by L
<221> NAME/KEY: VARIANT
<222> LOCATION: 1
<223> OTHER INFORMATION: may be replaced by S

<400> SEQUENCE: 3

Cys His Ser Lys Thr Arg
1               5

<210> SEQ ID NO 4
<211> LENGTH: 382
<212> TYPE: PRT
<213> ORGANISM: homo sapiens

<400> SEQUENCE: 4

Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
            20                  25                  30

Val Asn Ile Val Cys His Ser Lys Thr Arg Ser Asn Pro Glu Asn Asn
        35                  40                  45

Val Gly Leu Ile Thr Leu Ala Asn Asp Cys Glu Val Leu Thr Thr Leu
    50                  55                  60

Thr Pro Asp Thr Gly Arg Ile Leu Ser Lys Leu His Thr Val Gln Pro
65                  70                  75                  80

Lys Gly Lys Ile Thr Phe Cys Thr Gly Ile Arg Val Ala His Leu Ala
                85                  90                  95

Leu Lys His Arg Gln Gly Lys Asn His Lys Met Arg Ile Ile Ala Phe
```

-continued

```
                100                 105                 110
Val Gly Ser Pro Val Glu Asp Asn Glu Lys Asp Leu Val Lys Leu Ala
            115                 120                 125

Lys Arg Leu Lys Lys Glu Lys Val Asn Val Asp Ile Ile Asn Phe Gly
            130                 135                 140

Glu Glu Glu Val Asn Thr Glu Lys Leu Thr Ala Phe Val Asn Thr Leu
145                 150                 155                 160

Asn Gly Lys Asp Gly Thr Gly Ser His Leu Val Thr Val Pro Pro Gly
            165                 170                 175

Pro Ser Leu Ala Asp Ala Leu Ile Ser Ser Pro Ile Leu Ala Gly Glu
            180                 185                 190

Gly Gly Ala Met Leu Gly Leu Gly Ala Ser Asp Phe Glu Phe Gly Val
            195                 200                 205

Asp Pro Ser Ala Asp Pro Glu Leu Ala Leu Ala Leu Arg Val Ser Met
            210                 215                 220

Glu Glu Gln Arg His Ala Gly Gly Gly Ala Arg Arg Ala Ala Arg Ala
225                 230                 235                 240

Ser Ala Ala Glu Ala Gly Ile Ala Thr Thr Gly Thr Glu Asp Ser Asp
            245                 250                 255

Asp Ala Leu Leu Lys Met Thr Ile Ser Gln Gln Glu Phe Gly Arg Thr
            260                 265                 270

Gly Leu Pro Asp Leu Ser Ser Met Thr Glu Glu Glu Gln Ile Ala Tyr
            275                 280                 285

Ala Met Gln Met Ser Leu Gln Gly Ala Glu Phe Gly Gln Ala Glu Ser
            290                 295                 300

Ala Asp Ile Asp Ala Ser Ser Ala Met Asp Thr Ser Glu Pro Ala Lys
305                 310                 315                 320

Glu Glu Asp Asp Tyr Asp Val Met Gln Asp Pro Glu Phe Leu Gln Ser
            325                 330                 335

Val Leu Glu Asn Leu Pro Gly Val Asp Pro Asn Asn Glu Ala Ile Arg
            340                 345                 350

Asn Ala Met Gly Ser Leu Pro Pro Arg Pro Pro Arg Thr Ala Arg Arg
            355                 360                 365

Thr Arg Arg Arg Lys Thr Arg Ser Glu Thr Gly Gly Lys Gly
370                 375                 380
```

PROCESS FOR PRODUCING EGG YOLK WITH HIGH CONTENT OF AF-16

CROSS-REFERENCE TO RELATED APPLICATIONS

This application is a National Stage Entry of PCT/EP2016/064114, filed Jun. 20, 2016, which claims priority from Swedish patent applications 1551018-3, filed Jul. 10, 2015. The contents of these priority applications are incorporated herein by reference in their entirety.

FIELD OF INVENTION

The present invention relates to a process for producing an egg yolk with a very high content of antisecretory factor (AF) proteins, in particular with a very high content of AF protein fragment consisting essentially of the amino acid sequence as shown in SEQ.ID.NO. 1 (AF-16) and/or in SEQ.ID.NO. 2 (AF-8), said process comprising for at least 12 weeks feeding a poultry, such as a hen, an AF-16 inducing pelleted feed for poultry comprising at least 0.14% free tryptophan, or at least 1-2 g tryptophan/kg feed, and thereafter harvesting egg from said poultry, separating egg yolk from egg white, and alternatively spray-drying, fluid-bed drying, grinding, leaching, extracting, evaporating, membrane filtrating, and/or or freeze-drying said egg yolk.

The present invention further relates to said egg yolk with a very high content of antisecretory factor (AF) proteins and fragments thereof, produced according to the herein described process, and to their use for the preparation of functional food products and pharmaceutical products for the treatment and prophylaxis of abnormal physiological conditions caused e.g. by exceptionally high levels of body fluid discharge. The invention also relates to food products and pharmaceutical products so prepared.

Definitions

Proteins are biological macromolecules constituted by amino acid residues linked together by peptide bonds. Proteins, as linear polymers of amino acids, are also called polypeptides. Typically, proteins have 50-800 amino acid residues and hence have molecular weights in the range of from about 6,000 to about several hundred thousand Dalton or more. Small proteins are called peptides, polypeptides, or oligopeptides. The terms "protein", "polypeptide", "oligopeptide" and "peptide" may be used interchangeably in the present context. Peptides can have very few amino acid residues, such as between 2-50 amino acid residues (aa).

A "pharmaceutical composition", in the present context, refers to a composition comprising a therapeutically active amount of an antisecretory factor (AF) protein, optionally in combination with a pharmaceutically active excipient, such as a carrier or a vehicle. Said pharmaceutical composition is formulated for the appropriate route of administration, which may vary depending on the condition of the patient, as well as on other factors, such as age or preferred choice. A pharmaceutical composition comprising an antisecretory factor (AF) protein can serve as a drug delivery system. The pharmaceutical composition upon administration presents the active substance to the body of a human or an animal. Said pharmaceutical composition may be in the form of e.g. tablets, pills, lozenges, capsules, stool pills, gels, solutions, etc., but is not limited thereto.

The term "pharmaceutically active salt", refers to a salt of an antisecretory factor (AF) protein, peptide, or polypeptide, or a homologue and/or fragment thereof which may be any salt derived therefrom, based on so-called Hofmeiser's series. Other examples of pharmaceutically active salts comprise triflouroacetate, acetate, sulphate and chloride, the invention is not limited thereto.

The term "antisecretory" refers in the present context to inhibiting or decreasing secretion and/or fluid transfer. Hence, the term "antisecretory factor (AF) protein" refers to a class of proteins capable of inhibiting or decreasing or otherwise modulating fluid transfer as well as secretion in a body.

In the present context, "equivalent activity" relates to the biological effect of the antisecretory factor (AF) protein, peptide, or polypeptide, or a homologue, derivative and/or fragment thereof, i.e. its capacity for improving therapy and/or use in treating glioblastoma. Standardized examples for testing and/or measuring such a capacity are well known in the field of the art.

In the present context, the terms an "Antisecretory factor protein", "antisecretory factor (AF) protein", "AF-protein", AF, or a homologue, derivative or fragment thereof, may be used interchangeably with the term "antisecretory factors" or "antisecretory factor proteins" as defined in WO 97/08202, and refer to an antisecretory factor (AF) protein or a peptide or a homologue, derivative and/or fragment thereof having antisecretory and/or equivalent functional and/or analogue activity, or to a modification thereof not altering the function of the polypeptide. Hence, it is to be understood that an "antisecretory factor", "antisecretory factor protein", "antisecretory peptide", "antisecretory fragment", or an "antisecretory factor (AF) protein" in the present context, also can refer to a derivative, homologue or fragment thereof. These terms may all be used interchangeably in the context of the present invention. Furthermore, in the present context, the term "antisecretory factor" may be abbreviated "AF". Antisecretory factor (AF) protein in the present context also refers to a protein with antisecretory properties as previously defined in WO 97/08202 and WO 00/38535. Antisecretory factors have also been disclosed e.g. in WO 05/030246. Also intended by the term antisecretory factor are native and/or natural antisecretory factors in egg yolk enriched in antisecretory factors as disclosed in SE 900028-2 and WO 00/38535, as further described below.

Below, the term "NASP" will be used for "natural antisecretory protein".

The term "ASP" will be used for "antisecretory protein" comprised in natural antisecretory protein.

By "functional food product" is meant, in the present context, a food product having a salubrious function, i.e. having a beneficial effect on the health of man or an animal.

PBS: phosphate buffered saline;

AF: antisecretory factor,

Full-length AF protein (as shown in SEQ ID NO: 1)

AF-6: a hexa peptide CHSKTR (as shown in SEQ ID NO: 2);

AF-16: a peptide composed of the amino acids VCHSKTRSNPENNVGL (as shown in SEQ ID NO: 3);

AF-8: a septa peptide VCHSKTR (as shown in SEQ ID NO: 4);

Octa peptide IVCHSKTR (as shown in SEQ ID NO: 5);

Penta peptide HSKTR (as shown in SEQ ID NO: 6).

SPC: Specially Processed Cereals

RTT: Method for measuring a standardized secretion response in rat small intestine, as published in SE 9000028-2 (publication number 466331) for measuring content of AF (ASP).

BACKGROUND

WO 98/21978 discloses the use of products having enzymatic activity for the production of a food that induces the formation of antisecretory factor (AF) proteins. WO 00/038535 further discloses food products enriched in native antisecretory factor (AF) proteins as such.

From the Swedish Patent SE 9000028-2 (publication No. 466,331) it is known that the formation of an antisecretory factor or an antisecretory protein (ASP: also named FIL) can be stimulated by adding, to the animals' feed, certain sugars, amino acids and amides. The kinds and amounts of these substances to be used for the formation of an interesting amount of ASP is determined by a method disclosed in the patent. Briefly, this method involves measurement of a standardized secretion response in the small intestine of rat. From the patent is evident that the induced ASPs formed direct the secretion of body fluid into the intestine. In said patent, the content or amount of natural antisecretory proteins is defined by its effect on the fluid secretion into the small intestine of laboratory rats having been challenged with cholera toxin. One ASP unit (FIL unit) corresponds to a 50% reduction of the fluid flow in the intestine compared to a control without ASP. The antisecretory proteins are active in extremely small amounts and, therefore, it is easier to determine them by their effect than by their mass.

From the PCT application PCT/SE96/01049 the structures of certain antisecretory proteins are known, and their active parts are characterized. A synthetic ASP prepared by recombinant genetic engineering or by solid phase technology and having definite structures has been shown to have a general controlling influence on the body fluid flow over living cell membranes.

From the PCT application PCT/SE97/01918 (WO 98/21978) it is known that the formation of ASP can be induced in the body by consumption of a certain kind of food having enzymatic activity. The effect of the induction and, owing to that, the formation of ASP varies according to the individual and its symptoms and takes place with a strength and induction period unpredictable so far. However, they can be measured afterwards, and necessary corrections can be made with the guidance of said measurements.

During the inventors' continued work in formulating feed to stimulate the formation of antisecretory proteins in accordance with Swedish Patent SE 9000028-2, it was in known that the synthesis ability and concentrating of the natural antisecretory proteins formed are distributed most unevenly in the body. Very high levels of NASP were found in certain organs, body parts or body fluids and, in particular, in the yolk of birds' eggs. WO 008535 disclosed this fact and, consequently, the use of egg yolk having been enriched with regard to NASP. WO 008535 in general disclosed the preparation of NASP-enriched food products and pharmaceutical products for the treatment and prophylaxis of abnormal physiological conditions caused by extreme body fluid discharge.

BRIEF DESCRIPTION OF THE INVENTION

In contrast to the egg yolk previously described e.g. in WO 008535, the present invention for the first time describes egg yolk with a much higher content of antisecretory factor (AF) proteins and in particular, with a constant and high content of the factor (AF) protein fragment with an amino acid sequence as disclosed in SEQ.ID.NO.1 (AF-16) and/or in SEQ.ID.NO.2 (AF-8). The egg yolk disclosed herein comprises at least 0.05 ng/ml antisecretory factor (AF) protein fragment with an amino acid sequence as disclosed in SEQ.ID.NO.1 and/or in SEQ.ID.NO.2 (AF-8). The egg yolk can be in fluid form, or alternatively be spray-dried, or fluid bed dried, and is further characterized by inducing at least 0.5 AF-Units in a patient in need thereof between 60-120 min after intake of at least 4 grams of said freeze dried egg yolk, which is at least double as fast as could be induced by the egg yolk described in WO008535.

The egg yolk according to the present invention can typically originate from eggs of poultry, such as from gallinaceous birds, such as from a hen.

The egg yolk according to the present invention is produced by a process for producing an egg yolk with a very high content of antisecretory factor (AF) proteins, in particular with a very high content of AF protein fragment as shown in SEQ.ID.NO. 1 (AF-16), said process comprises for at least 12 weeks feeding a poultry, such as a hen, an AF-16 inducing pelleted feed for poultry comprising at least 0.4% free tryptophan and thereafter harvesting egg from said poultry, separating egg yolk from egg white, and alternatively spray-drying, fluid bed drying, grinding, leaching, extracting, evaporating, membrane filtrating, and/or or freeze-drying said egg yolk.

In one embodiment, the egg yolk according to the present invention is produced by a process for producing an egg yolk with a very high content of antisecretory factor (AF) proteins, in particular with a very high content of AF protein fragment as shown in SEQ.ID.NO. 2 (AF-8), said process comprises for at least 12 weeks feeding a poultry, such as a hen, an AF-8 inducing pelleted feed for poultry comprising at least 0.4% free tryptophan and thereafter harvesting egg from said poultry, separating egg yolk from egg white, and alternatively spray-drying, fluid bed drying, grinding, leaching, extracting, evaporating, membrane filtrating, and/or or freeze-drying said egg yolk.

The egg yolk according to the present invention is produced by a process for producing an egg yolk with a very high content of antisecretory factor (AF) proteins, in particular with a very high content of AF protein fragment as shown in SEQ.ID.NO. 1 (AF-16) and/or in SEQ.ID.NO.2 (AF-8), said process comprises for at least 12 weeks feeding a poultry, such as a hen, an AF-16 and/or AF-8 inducing pelleted feed for poultry comprising at least 0.4% free tryptophan and thereafter harvesting egg from said poultry, separating egg yolk from egg white, and alternatively spray-drying, fluid bed drying, grinding, leaching, extracting, evaporating, membrane filtrating, and/or or freeze-drying said egg yolk.

In one embodiment of the present invention, the egg yolk produced by the process according to the present invention is used in medicine. In a presently preferred embodiment, said egg yolk is used in the treatment and prophylaxis of disease-like conditions caused by extreme body fluid discharge, selected from the group of diseases but not limited to the group consisting of diarrhea, inflammatory diseases, edemas, autoimmune diseases, cancer, tumors, leukemia, diabetes, diabetes mellitus, glioblastoma, Alzheimer's Disease, Parkinsons' Disease, Encephalitis, and Meniere's Disease.

In a presently equally preferred embodiment, said egg yolk is used for use in optimizing compartmental and/or cellular drug up-take, for neuroprotection.

The present invention is also directed to the use of the egg yolk produced by the process according to the present invention, for the preparation of a medicament for the treatment and/or prophylaxis of disease-like conditions caused by extreme body fluid discharge, diarrhea, inflammatory diseases, cancer, glioblastoma, AD, and/or PD. The present invention is also directed to the use of the egg yolk produced by the process according to the present invention for the preparation of a medicament for optimizing compartmental and/or cellular drug up-take and/or for neuroprotection.

The present invention is also directed to a method for the treatment and/or profylaxis of disease-like conditions caused by extreme body fluid discharge, diarrhea, inflammatory diseases, cancer, glioblastoma, AD, and/or PD, said method comprising administering a pharmaceutically effective amount of the egg yolk produced by the process according to the present invention to a subject in need thereof. The present invention is also directed to a method for optimizing compartmental and/or cellular drug up-take and/or for neuroprotection, said method comprising administering a pharmaceutically effective amount of the egg yolk produced by the process according to the present invention to a subject in need thereof.

An egg yolk according to the present invention can be used for the preparation of antisecretory factor (AF) protein-enriched functional food products, such as feed, food and/or food-supplements. Consequently, said food, feed and/or food-supplement comprising egg yolk according to the present invention is equally disclosed. Such a food comprising egg yolk according to the present invention can be selected from the group consisting of pancake, omelet, ice cream, hard- or soft-boiled egg and soft-drinks, yoghurt, foodbars etc.

Another embodiment of the present invention relates to a pharmaceutical composition comprising egg yolk according to the present invention and a suitable pharmaceutical carrier. Typically, the suitable pharmaceutical carrier is selected from the group consisting of water, PBS, etc.

One particular embodiment relates to a pharmaceutical composition comprising egg yolk according to the present invention, comprising 0.00005 ng/ml antisecretory factor (AF) protein fragment with an amino acid sequence as disclosed in SEQ.ID.NO.1. which is further characterized by inducing at least 0.5 AF-Units in a patient in need thereof.

The present invention relates to a process for producing an egg yolk with a very high content of antisecretory factor (AF) proteins, in particular with a very high content of AF protein fragment consisting essentially of the amino acid sequence as shown in SEQ.ID.NO.1 (AF-16) and/or in SEQ.ID.NO. 2 (AF-8), said process comprising for at least 12 weeks feeding a poultry, such as a hen, an AF-16 and/or AF-8 inducing pelleted feed for poultry comprising at least 0.14% free tryptophan and thereafter harvesting egg from said poultry, separating egg yolk from egg white, and alternatively spray-drying, grinding, leaching, extracting, evaporating, membrane filtrating, fluid bed drying and/or freeze-drying said egg yolk. Said poultry is typically a gallinaceous bird such as a hen.

A process for producing an egg yolk according to the present invention can alternatively comprise feeding a poultry an AF-16 and/or AF-8 inducing feed for at least 13 or 14 weeks, such as for at least 15, 16, 17 or 18 weeks.

Consequently, the present invention also relates to AF-16 and/or AF-8 inducing feed for poultry usable in the process described herein, wherein said feed can further comprise amino acids, sugars and amides, and/or malted cereals in amounts and proportions such that the formation of AF-16 and/or AF-8 is stimulated in the poultry after consumption of said feed.

In one embodiment of the present invention, said AF-16 and/or AF-8 inducing feed for poultry comprises at least 0.14-1% free tryptophan, such as at least 0.7% or at least 0.1% free tryptophan and is in a pelleted form. The egg yolk produced according to the herein described process is in a presently preferred embodiment further characterized in that it comprises at least 0.05 ng/ml antisecretory factor (AF) protein fragment with an amino acid sequence as disclosed in SEQ.ID.NO.1. In another embodiment, the egg yolk produced according to the herein described process is further characterized in that it comprises at least 0.05 ng/ml antisecretory factor (AF) protein fragment with an amino acid sequence as disclosed in SEQ.ID.NO.2.

DETAILED DESCRIPTION OF THE INVENTION

Egg Yolk

Figure 1:
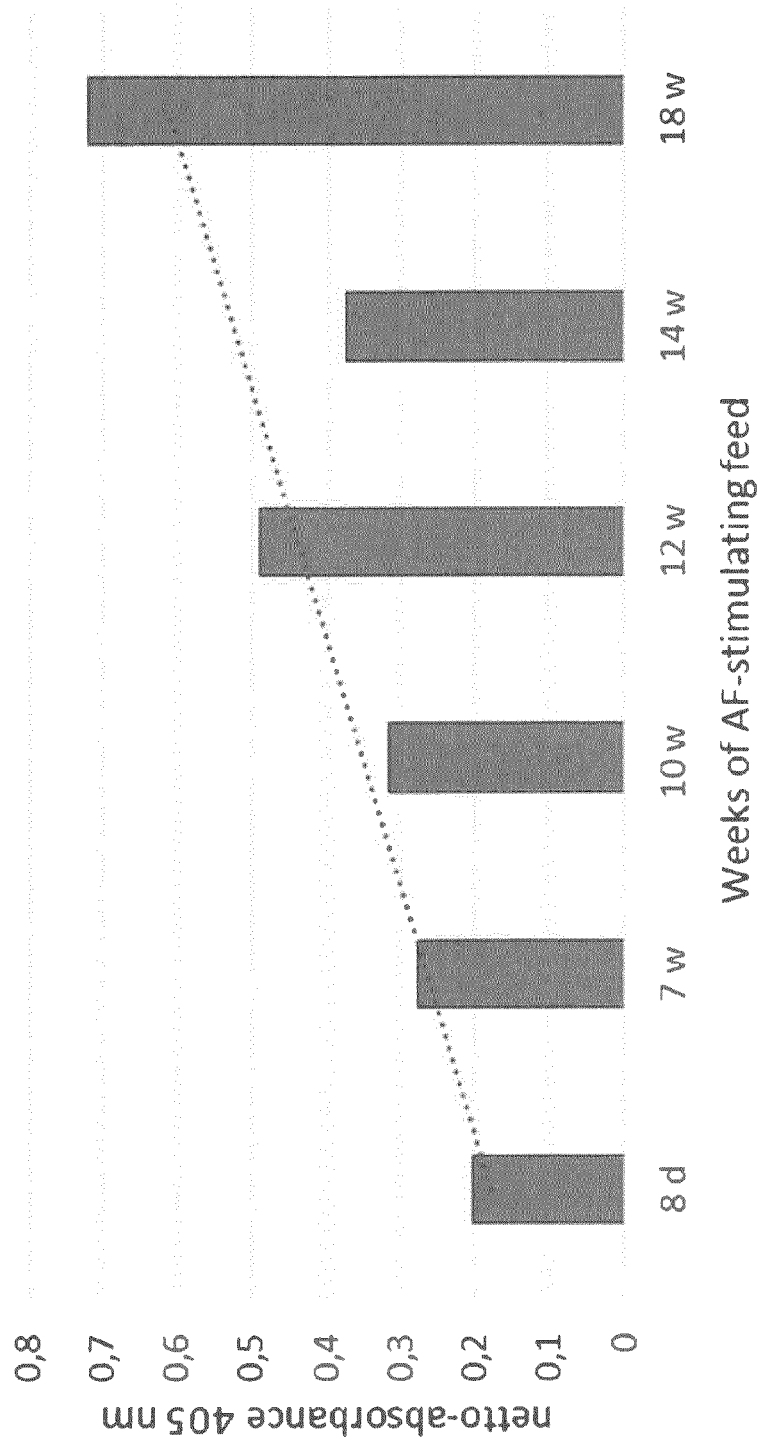
FIG. 1 shows the level of AF-16 in affinity-purified egg yolk as tested by ELISA using aP8.

The egg yolk produced according to the herein described process is in a presently preferred embodiment further characterized in that it comprises at least 0.05 ng/ml antisecretory factor (AF) protein fragment with an amino acid sequence as disclosed in SEQ.ID.NO.1 and/or in SEQ.ID.NO.2.

Food and Food-Supplements

The present invention generally relates to use of egg yolk for the preparation of antisecretory factor (AF) protein, such as in particular AF-16-enriched functional food products and pharmaceutical products for the treatment and prophylaxis of abnormal physiological conditions caused by extreme body fluid discharge.

According to another aspect the invention relates to such use for the preparation of provisions for particular nutrient purposes and pharmaceutical products containing antisecretory factor (AF) proteins, such as in particular AF-16 and/or AF-8.

The expression "food product" is intended, in the present context, to comprise food for human use as well as feed for animal use. The food can be an article in the form of products, the preparation of which includes egg yolk, such as pancake, omelet, ice-cream and various kinds of bread. The egg yolk may also be consumed in the form of egg-nog or hard-boiled or soft-boiled eggs. The food can also be in the form of bread, biscuits, pasta, grains and flakes, porridge or gruel, or mixed into various beverage compositions with or without electrolytes, or a food preparation containing meat and meat products, fat and fat products or milk and milk products having been enriched with antisecretory factor (AF) protein, such as in particular AF-16 and/or AF-8. Antisecretory factor (AF) protein, such as in particular AF-16 and/or AF-8 can be mixed into the food product in a more or less purified form. The food preparation can be made up with great liberty using knowledge known to the skilled man, in order to comply with requirements as regards palatability and meal variation.

The egg yolk typically originates from birds' eggs that can be used for human and animal consumption and which comprise a very high content of antisecretory factor (AF) protein, such as in particular AF-16 and/or AF-8. The eggs are preferably produced by laying hens but can also be obtained from e.g. ducks, turkey, quail and ostrich.

A food or feed with a very high content of antisecretory factor (AF) protein, such as in particular AF-16 and/or AF-8 comprises said protein or protein fragment in a concentration such that, when consuming the food product, it provides the desired valuable effect on health.

In one embodiment, consumption of at least 4 g egg yolk produced according to the presently disclosed process induces in the patient in need thereof at least 0.5 AF-Units in said patient's blood, i.e. the level of FIL units/ml of blood exceeds 0.5 FIL units/ml of blood. Healthy people typically have AF-Unit levels in blood between 0 and 0.5 FIL Units/ml of blood.

When stimulating the antisecretory factor (AF) protein, such as in particular AF-16 and/or AF-8 production it has been shown, surprisingly and unexpectedly, that extremely high levels of antisecretory factor (AF) protein, including fragments thereof, such as in particular AF-16 and/or AF-8 can be induced in birds' eggs.

Pharmaceutical Compositions

The antisecretory factor (AF) protein, and fragments thereof, such as in particular AF-16 and/or AF-8 produced in the egg yolk can be concentrated, e.g. on a specific adsorbing column, eluted, recovered and/or concentrated and can thereafter be administered to animal or humans, mixed with a feed or food, respectively, or as more or less isolated products, prepared and formulated as pharmaceuticals or other health-providing products. Such pharmaceutical products are prepared in a manner known to the skilled man, using accepted excipients including carriers and diluents and are formulated as solid or liquid forms dependent on the intended administration route.

The pharmaceutical compositions envisioned herein are preferably formulated for oral intake and administered orally.

According to another embodiment of the use in accordance with the invention for the preparation of antisecretory factor (AF) protein-, and/or fragments thereof, such as in particular AF-16- and/or AF-8-enriched food products, use is made of the egg yolk as such or of the complete egg, possibly in processed form, for mixing with the food or feed. Any processing can include grinding, leaching, extraction, evaporation, ultra-filtration, drying and other standard operations in order to obtain an antisecretory factor (AF) protein-, such as in particular AF-16- and/or AF-8-enriched egg yolk product, suitable for practical purposes, for mixing with the food or feed.

Typically, antisecretory factor (AF) protein, such as in particular AF-16 and/or AF-8, is administered in doses of 4 g-8 g spray-dried egg-yolk powder once or twice daily.

For certain conditions even higher doses of antisecretory factor (AF) protein, such as in particular AF-16 and/or AF-8 may be required. In such cases, antisecretory factor (AF) protein, such as in particular AF-16 and/or AF-8 isolated from the egg yolk can be added to any food product or isolated antisecretory factor (AF) protein, such as in particular AF-16 and/or AF-8, can be prepared for intake in the form of tablets or suspensions.

A particularly preferred embodiment comprises the preparation of egg yolk powder by spray-drying. Such a product is particularly well suitable in industrial processing of various food products where it is desired to achieve the beneficial effect of antisecretory factor (AF) protein, such as in particular AF-16 and/or AF-8, upon intake of the food product in question. The egg yolk powder lets itself be well mixed into such greatly differing products as sausage and ice cream, owing to which a far-reaching variation as regards meal character will be possible to achieve.

The egg yolk powder is also most suitable as intermediate in case it is desired to prepare an enriched or concentrated antisecretory factor (AF) protein, such as in particular AF-16 and/or AF-8 product through leaching or extraction for later preparation of e.g. pharmaceuticals.

Owing to its relatively low molecular weight, antisecretory factor (AF) protein, and in particular fragments thereof, such as AF-16 and/or AF-8, is comparatively heat-stable and can therefore be contained in the food already before preparing the same for consumption.

In one embodiment of the present invention, the pharmaceutical composition according to the invention further comprises a pharmaceutically acceptable excipient. The choice of pharmaceutically acceptable excipient and their optimum concentration for use according to the present invention can readily be determined by the skilled person by experimentation. Pharmaceutically acceptable excipients for use according to the present invention include solvents, buffering agents, preservatives, chelating agents, antioxidants, and stabilizers, emulsifying agents, suspending agents and/or diluents. The pharmaceutical compositions of the invention may be formulated according to conventional pharmaceutical practice, e.g. according to "Remington: The science and practice of pharmacy", 21st edition, ISBN 0-7817-4673-6 or "Encyclopedia of pharmaceutical technology", 2nd edition, ed. Swarbrick J., ISBN: 0-8247-2152-7. A pharmaceutically acceptable excipient is a substance that is substantially harmless to the individual to which the composition is to be administered. Such an excipient normally fulfills the requirements given by the national health authorities. Official pharmacopoeias such as e.g. the British Pharmacopoeia, the United States of America Pharmacopoeia and The European Pharmacopoeia set standards for pharmaceutically acceptable excipients.

The following is a review of relevant compositions for optional use in a pharmaceutical composition according to the invention. The review is based on the particular route of administration. However, it is appreciated that in those cases where a pharmaceutically acceptable excipient may be employed in different dosage forms or compositions, the application of a particular pharmaceutically acceptable excipient is not limited to a particular dosage form or of a particular function of the excipient. It should be emphasized that the invention is not limited to the use of the compositions mentioned in the following.

Parenteral Compositions:

For systemic application, the compositions according to the invention may contain conventional non-toxic pharmaceutically acceptable carriers and excipients, including micro spheres and liposomes.

The compositions for use according to the invention may include all kinds of solid, semi-solid and fluid compositions.

The pharmaceutically acceptable excipients may include solvents, buffering agents, preservatives, chelating agents, antioxidants, and stabilizers, emulsifying agents, suspending agents and/or diluents.

The pharmaceutical composition according to the invention can in one context be administrated locally or via intravenous peripheral infusion or via intramuscular or subcutaneous injection into the patient or via buccal, pulmonary, nasal, cutaneous or oral routes. Furthermore, it is also possible to administer the pharmaceutical composition through a surgically inserted shunt into a cerebral ventricle of the patient.

In one embodiment, the pharmaceutical composition used according to the present invention is formulated for intraocular, local, intranasal, oral, subcutaneous and/or systemic administration. The chosen route of administration will vary depending on the condition of the patient to be treated and the patient's age and gender etc. In a preferred embodiment, the composition of the invention is administrated by application as a suspension or, even more preferably, a powder for inhalation with a spray, aerosol, inhaler or nebulizer nasally and/or to the respiratory tract.

The administration of a powder comprising antisecretory factors has the additional advantages in terms of stability and dosage. A pharmaceutical composition according to the invention can also be topically applied, ocularly, nasally, orally, subcutaneously and/or systemically administered via blood vessels. In a preferred embodiment, the pharmaceutical composition is formulated for intravenous, intramuscular, local, oral or nasal administration. Typically, when used for topical application to the eye, the applied concentration in the composition of the invention is from 1 µg to 1 mg per application, preferably 50-500 µg, either as a single dose per day or repeated several times per day (multiple doses), but is not limited thereto.

Systemically administrated to the blood, the dose is within the range of 0.1 µg to 10 mg per application and kg body weight, such as 0.1 µg to 1 mg per application and kg body weight, preferably 1-500, such as 1-1000 µg/kg body weight. When egg yolk enriched in antisecretory factors is used according to the present invention, this formulation is preferably administered orally.

In one embodiment of the invention, said pharmaceutical composition further comprises a pharmaceutically acceptable excipient. Such an excipient may be any preferable excipient chosen to be appropriate for the specific purpose.

Antisecretory Factor (AF)

The antisecretory factor is a class of proteins that occurs naturally in the body. Antisecretory factor (AF) is a 41 kDa protein that originally was described to provide protection against diarrhea diseases and intestinal inflammation (for a review, see Lange and Lönnroth, 2001). The antisecretory factor (AF) protein has been sequenced and its cDNA cloned. The human antisecretory factor AF protein is a 41 kDa protein, comprising 382-288 amino acids when isolated from the pituitary gland. The active site with regard to the beneficial effect on treatment of glioblastoma according to the present invention can be localized to the protein in a region close to the N-terminal of the protein, in particular localized to amino acids 1-163 of SEQ ID NO 4, more specifically to amino acid positions 35-50 on the antisecretory factor (AF) protein sequence. The biological effect of AF is exerted by any peptide or polypeptide comprising at least 6 amino acids, SEQ ID NO: 3 (AF-6), of said consensus sequence, or a modification thereof not altering the function of the polypeptide and/or peptide.

Immunochemical and immunohistochemical investigations have revealed that the antisecretory factor (AF) protein is present and may also be synthesized by most tissues and organs in a body. Synthetic peptides, comprising the antidiarrhoeic sequence, have prior been characterized (WO 97/08202; WO 05/030246).

The present inventors have shown that the antisecretory factor is to some extent homologous with the protein S5a and Rpn10, which constitutes a subunit of a constituent prevailing in all cells, the 26 S proteasome, more specifically in the 19 S/PA 700 cap. In the present invention, antisecretory factor (AF) proteins are defined as a class of homologue proteins having the same functional properties. Antisecretory factor is also highly similar to angiocidin, another protein isoform known to bind to thrombospondin-1 and associated with cancer progression.

Homologues, derivatives and fragments of antisecretory factor (AF) proteins and/or peptides according to the present invention all have analogous biological activity. Homologues, derivatives and fragments, in the present context, comprise at least 6 amino acids (as shown in SEQ ID NO: 2) corresponding to those of a naturally occurring antisecretory factor (AF) protein, which may be further modified by changing one or more amino acids in order to optimize the antisecretory factor's biological activity, without altering the essential function of the polypeptide and/or peptide.

By a derivative is in the present context intended a protein having equivalent activity and/or a functional equivalent activity to an antisecretory factor as defined herein, being derived from another substance either directly or by modification or partial substitution, wherein one or more amino acids have been substituted by another amino acid, which amino acid can be a modified or an unnatural amino acid. For example, the antisecretory factor derivatives according to the invention may comprise an N terminal and/or a C terminal protecting group. One example of an N terminal protecting group includes acetyl. One example of a C terminal protecting group includes amide.

Furthermore, any amino acid sequence being at least 70% identical, such as being at least 72%, 75%, 77%, 80%, 82%, 85%, 87%, 90%, 91%, 92%, 93%, 94%, 95%, 96%, 97%, 98%, or 99% identical with the amino acid sequence of an antisecretory factor (AF) protein, peptide, homologue, derivative and/or fragment according to the invention, is also considered to be inside the scope of the present invention.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al, Altschul, S. F. et al (1990)). Each sequence analysis program has a default scoring matrix and default gap penalties. In general, a molecular biologist would be expected to use the default settings established by the software program used.

The antisecretory factor (AF) proteins or a peptide or a homologue, derivative and/or fragment thereof having equivalent activity as defined herein, can comprise 6 amino acids or more, such as 6-16 amino acids, such as 6, 7, 8, 9, 10, 11, 12, 13, 14, 15, 16, 17, 18, 19 or 20 amino acids or more. In other preferred embodiments the antisecretory factor consists of 42, 43, 45, 46, 51, 80, 128, 129 or 163 amino acids. In preferred embodiments the antisecretory factor (AF) protein, a homologue, derivative, peptide and/or fragment thereof, according to the present invention consists of 6, 7, 8 or 16 amino acids.

In particular, an antisecretory factor (AF) protein is a protein with an amino acid sequence as shown in SEQ ID NO:2, or a homologue, derivative and/or fragment thereof comprising amino acids 37-42 of SEQ ID NO:2.

AF-16 is a fragment of an antisecretory factor (AF) protein with an amino acid sequence as shown in SEQ ID NO:1, thus comprising amino acids 37-42 of SEQ ID NO:2.

Medical Indications

Antisecretory factor (AF) protein, such as in particular AF-16, has been shown to have a generally controlling effect on the body fluid flow over living cell membranes, owing to which not only diarrhoea conditions can be alleviated, cured or prevented but also discomfort due to physiological unbalance or disease-like conditions caused by extreme body fluid discharge such as inflammations, edema, arthritis, glaucoma and other changes in the body, such as migraine, burns and traumatic injuries in and on the body.

The food products and the pharmaceutical products according to the invention can be used for such a purpose.

The food products and the pharmaceutical products according to the invention can be used as an adjuvant for the treatment of glioblastoma and/or for optimizing delivery and cellular uptake of a pharmaceutical substance and/or formulation, such as an anticancer drug, immune therapy, radiation therapy or a gene delivery to a glioblastoma tumor cell.

Antisecretory factor (AF) proteins and peptides have previously been disclosed to normalize pathological fluid transport and/or inflammatory reactions, such as in the intestine and the choroid plexus in the central nervous system after challenge with the cholera toxin (WO 97/08202). The food products and the pharmaceutical products according to the invention can be used for such a purpose.

Food and feed with the capacity to either induce endogenous synthesis of AF or uptake of added AF have been suggested to be useful for the treatment of edema, diarrhea, dehydration and inflammation in WO 97/08202. The food products and the pharmaceutical products according to the present invention can be used for such a purpose.

Antisecretory factor (AF) proteins and fragments thereof have also been shown to improve the repair of nervous tissue, and proliferation, apoptosis, differentiation, and/or migration of stem and progenitor cells and cells derived thereof in the treatment of conditions associated with loss and/or gain of cells (WO 05/030246) and to be equally effective in the treatment and/or prevention of intraocular hypertension (WO 07/126364), as for the treatment and/or prevention of compartment syndrome (WO 07/126363). The food products and the pharmaceutical products according to the present invention can be used for such a purpose.

What is more, the present inventors recently showed that AF is able to monitor and/or beneficially affect the structure, distribution and multiple functions of lipid rafts, receptors and/or caveolae in membranes and could thus be employed for the treatment and/or prevention of structural disorganization and dysfunction of lipid rafts and/or caveolae in cell membranes (WO 07/126365). The food products and the pharmaceutical products according to the present invention can be used for such a purpose.

The present inventors have further been able to prove that the same antisecretory factor (AF) protein, peptides and fragments thereof can intervene in the biological activation of transmembrane proteins, e.g. NKCC1 through FAK and CAP, and that they can thus directly regulate the pathological activity of the ion channel in pathological and/or perturbed cells, effectively normalizing the intracellular pressure and transmembrane protein function in said cell, and thus allowing an improved uptake of drugs used in e.g. cancer therapy (WO 2010/093324). The food products and the pharmaceutical products according to the present invention can be used for such a purpose.

WO 2014/096384 discloses that antisecretory factor (AF) proteins, peptides, homologues and/or fragments thereof can further be used both in symptomatic, curative and palliative therapies for glioblastoma. In particular, they can be used as an adjuvant and/or to optimize drug and gene delivery, as well as chemotherapy, immunotherapy and radiotherapy in the treatment of glioblastoma. The food products and the pharmaceutical products according to the present invention can be used for such a purpose.

Process

One aspect of the present invention relates to a process for providing egg yolk from birds' eggs with a very high content of antisecretory factor (AF) proteins, in particular with a very high content of AF protein fragment consisting essentially of the amino acid sequence as shown in SEQ.ID.NO.1 (AF-16) and/or in SEQ.ID.NO. 2 (AF-8), said process comprising for at least 12 weeks feeding a poultry, such as a hen, an AF-16 and/or AF-8 inducing, preferably pelleted, feed for poultry comprising at least 0.14% free tryptophan, such as at least 0.4% free tryptophan, and thereafter harvesting egg from said poultry, separating egg yolk from egg white, and alternatively spray-drying, fluid bed drying, grinding, leaching, extracting, evaporating, membrane filtrating, and/or or freeze-drying said egg yolk.

In particular, the process of the invention is applicable when feeding gallinaceous birds with an AF-16 and/or AF-8 inducing pelleted feed for poultry as described for the first time herein for at least 12 weeks, preferably between 12-20 weeks, such as between 12-18 weeks, such as at least 12, 13, 14, 15, 16, 17, 18, 19 or 20 weeks. By providing, via the feed, during at least 12 weeks, the hens with distinct combinations of amino acids, sugars and amides very high levels of antisecretory factor (AF) proteins, and in particular AF-16 and/or AF-8 can be induced, preferably in the egg yolk.

In another embodiment, the process of the invention is applicable when feeding gallinaceous birds with an AF-16 and/or AF-8 inducing pelleted feed for poultry as described for the first time herein for at least 4 weeks, such as least 4, 5, 6, 7, 8, 9, 10, 11, 12, 13, 14, 15, 16, 17, 18, 19 or 20 weeks, such as preferably between 4-12 weeks. By providing, via the feed, during at least 4 weeks, the hens with distinct combinations of amino acids, sugars and amides very high levels of antisecretory factor (AF) proteins, and in particular AF-16 and/or AF-8 can be induced, preferably in the egg yolk.

The herein achieved very high levels of antisecretory factor (AF) proteins, and in particular AF-16 and/or AF-8, are unprecedented and surprising.

The invention is illustrated below by means of the following non-limiting examples.

AF-16 and/or AF-8 Inducing Pelleted Feed for Poultry

In the herein described process for providing egg yolk from birds' eggs with a very high content of antisecretory factor (AF) proteins, in particular with a very high content of AF protein fragment consisting essentially of the amino acid sequence as shown in SEQ.ID.NO.1 (AF-16) and/or SEQ.ID.NO. 2 (AF-8), said process comprises for at least 4, such as at least 12 weeks feeding a poultry, such as a hen, an AF-16 and/or AF-8 inducing pelleted feed for poultry comprising at least 0.14% free tryptophan or between 1-2 gram tryptophan/kg feed.

In one embodiment of the present invention, said AF-16 and/or AF-8 inducing feed for poultry comprises at least 0.14-1% free tryptophan, such as at least 0.2, 0.3, 0.4, 0.5, 0.6, 0.7, 0.8, 0.9, or 1% free tryptophan.

In one embodiment of the present invention, said AF-16 and/or AF-8 inducing feed for poultry comprises at least 0.5 gram tryptophan/kg feed, such as at least 0.5, 0.6, 0.7, 0.8, 0.9, 1.0, 1.1, 1.2, 1.3, 1.4, 1.5, 1.6, 1.7, 1.8, 1.9, 2.0, 2.2, 2.3, 2.4, 2.5, 2.6, 2.7, 2.8, 2.9 or 3% tryptophan/kg feed.

The feed is preferably in a pelleted form. The term "pelleted feed" is in the present context used to describe concentrated foods made into pellets. The pellets have the advantages of ease of handling, lack of dust and waste, and rendering of a standard composition of the pellets.

In the present context, the term "feed" is used to describe materials of nutritional value fed to animals. Each species has a normal diet composed of feeds or feedstuffs which are appropriate to its kind of alimentary tract and which are economically sensible as well as being nutritious and palatable. Agricultural animals at pasture have a diet which is very variable and subject to naturally occurring nutritional deficiencies.

One method of supplying the free tryptophan and other supplements and additives is to prepare a mix of these substances which is added to the basic ration. These mixes are called concentrates or premixes and, because they usually have a high content of cereal grains, mixes that contain only grain are also called concentrates. In the present context, such a premix typically comprises at least 2.5% free tryptophan, 70-75% sugar, such as dextrose and 25-30% cereal-based substrate, e.g wheat.

The presently disclosed feed can further comprise forage feed, such as hay, ensilage, green chop. I.e. any feed with a high cellulose content relative to other nutrients.

The presently disclosed feed can further comprise feed grain, such as cereal and other grains and pulses used as animal feed, including wheat, barley, oats, rye, maize, peas, raps, rape seed, rape seed meal, soybean meal, and sorghum.

The presently disclosed feed can further comprise feed supplements, i.e. nutritive materials which are feedstuffs in their own right and which are added to a basic diet such as pasture to supplement its deficiencies, such as minerals and aromatics. Feed supplements typically include trace elements and macrofeeds, such as protein supplements.

REFERENCES

1. Lange S. A rat model for an in vivo assay of enterotoxic diarrhea. FEMS Microbiol Lett 1982; 15:239-42.
2. Bjorck S, Bosaeus I, Ek E, Jennische E, Lonnroth I, Johansson E, Lange S. Food-induced stimulation of the antisecretory factor can improve symptoms in human inflammatory bowel disease: a study of a concept. Gut 2000; 46:824-9.
3. Goransson L, Lange S, Lonnroth I. Postweaning diarrhea: focus on diet. Pigs News and Information 1995; 16:89N-91N.
4. Lange S, Lonnroth I. The antisecretory factor: synthesis, anatomical and cellular distribution, and biological action in experimental and clinical studies. Int Rev Cytol 2001; 210:39-75.
5. Zaman S, Aamir K, Lange S, Jennische E, Silferdal S A, Hanson L A. Antisecretory factor effectively and safely stops childhood diarrhoea: a placebo-controlled, randomized study. Acta Paediatr 2014; 103:659-664.
6. Zaman S, Mannan J, Lange S, Lonnroth I, Hanson L A. B 221, a medical food containing antisecretory factor reduces child diarrhoea: a placebo controlled trial. Acta Paediatr 2007; 96:1655-9.
7. Lange S, Lonnroth I, Martinsson K. Concentrations of antisecretory factor in eggs and in chicken blood plasma. Br Poult Sci 1994; 35:615-620.

Experiments

Experiment 1

Detection and Relative Quantification of AF-16 in Salovum® using ELISA and MALDI-MS Methods and Materials Production of Salovum®, Technical Aspects After an adequate, antisecretory concentration of AF activity had been determined in vivo in the egg yolk by means of the rat ligated loop assay, eggs were collected and stored at +4° C. The yolk was then separated from the white, pasteurized, and then stored in sterile chambers and then spray-dried in a room with filtered air. The whole process took place under conditions securing exclusion of protein denaturation. In a final moment the spray dried egg yolk was packed in sachets, each containing 4 grams egg yolk powder. Salovum® can easily be dissolved at room temperature in water or juice, and can preferably be administered in pine apple juice which completely eliminated the taste of eggs.

Preparation of Egg Yolk-AF

Salovum® egg yolk, after serial AF induction, and also egg yolk prepared from control hens with a low content of AF, were dissolved (pool of four yolks) in phosphate buffered saline (PBS), centrifuged at 1000×g for 5 min and the supernatant collected. AF was purified from egg yolk, using affinity-chromatography (Bjorck et al, 2000). In brief, after passage of the egg yolk supernatant through a 3 ml agarose column (Sepharose 6B, GE Healthcare Bio-sciences AB) and washing in PBS, the agarose-absorbed AF was eluted with 1 M methyl-a-D-glucoside. The eluate was dialyzed against PBS for 24 h at 4° C. and then stored at −20° C. until use.

Determination In Vivo of AF Activity in Egg Yolk

The AF activity of the purified egg yolk fraction was determined by the ligated loop assay in rats using cholera toxin (CT) as a secretagogue (1). Thus, an AF preparation mediating a 50% inhibition of CT-induced fluid secretion in a jejunal rat loop, was assigned an "AF-unit" value of 0.5. Previous studies on humans (2) and animals (3) have shown that AF values >0.5 AF units are correlated with reduction of diarrhea secretion (2).

AF-16 Antibody

Primary polyclonal antibody against the AF peptide $^{36}$-VCHSKTRSNPENNVGL-$^{51}$ was raised in rabbit (aP8). The peptide was produced by means of organic chemical synthesis on solid phase and the following production of antiserum was made by Innovagen AB (Lund, Sweden).

ELISA test of Immunogenic AF-16.

The content of AF-16 in egg yolk was assayed in an enzyme-linked immunosorbent assay (ELISA). The affinity purified egg yolk samples were titrated in Maxisorp microtiter plates (Nunc) and incubated overnight at 4° C. After blocking with 0.2% bovine serum albumin (BSA) in PBS for 45 min at 37° C., plates were washed with PBS+0.05% Tween 20 (PBS-T). The polyclonal antibody raised against AF peptide AF-16, aP8 (diluted 1/500 in PBS+0.05% Tween 20+0.2% BSA) was added and the plates were incubated for 2 h at room temperature (RT). After washing, alkaline phosphate (AP)-conjugated goat anti-rabbit immunoglobulin IgG (Jackson ImmunoResearch Europe Ltd.) was added for 1 h at RT. After washing, the substrate 4-Nitrophenyl phosphate (Sigma-Aldrich Sweden AB) in diethanolamine buffer (pH9.8) with 1 mM MgCl$_2$ was added to the plates and the bound enzyme was revealed by reading absorbance at 405 nm. Rabbit pre-immune serum was used as background and the values were deducted to give the net absorbance.

MALDI Mass Spectrometry Detection of AF-16

Relative Quantification of AF-16 peptide in affinity purified Egg Yolk Samples was tested by Matrix Assisted Laser Desorption Ionization Mass Spectrometry (MALDI-MS). 2 Different AutoXecute methods with 30000 and 10000 satisfactory was used to collect data from each sample deposited on the MALDI ground steel plate with %80 laser intensity and hexagon raster movement. HCCA was used as the matrix solution and signal intensities of AF-16 were normalized to the matrix signal 568.2 (3HCCA+H). To test the method we added a dilution series of AF-16 in egg yolk samples after affinity chromatography and applied the same method collecting 30000 satisfactory shots.

Results

Egg Yolk Tested for Biological Activity

Purified egg-yolk samples were tested for AF activity in the rat ligated loop assay. The yolk was collected from eggs each week during hen intake of a diet stimulating to high endogenous AF production. The results in Table 1 demonstrate increased AF activity for up to 14-15 weeks of diet intake, whereafter no further increase of AF activity could be registered by means of the in vivo assay. The eggs were finally collected after a continuous intake for 18 weeks of the AF-stimulating feed. In these eggs a significant AF activity could be determined in yolk samples diluted 1:1000 (Table 1).

TABLE 1

AF activity in purified egg-yolk samples collected from hens after 2-3, 8-9 and 14-18 weeks after intake of an AF-inducing diet. A value of >0.5 AF-units correlates to a significantly diminished diarrhea output.

| Test group | Weeks of AF-Inducing diet | N | AF-units Means ± SEM* | Yolk dilution In test |
|---|---|---|---|---|
| A | 2-3 | 6 | 0.2 ± 0.01 | |
| B | 8-9 | 6 | 0.6 ± 0.02 | |
| | 14-18 | 8 | 0.5 ± 0.02 | 1:1000 |

Significance: A vs. B, P=0.0025

A vs. C, P=0.0123

B vs. C, P=NS

Egg Yolk Tested by ELISA

To evaluate the effect of AF induction after different time points, the content of AF-16 was determined with aP8. As shown in FIG. 1, the level was low in the samples prepared after up to 10 weeks of induction to reach a more than double increased level after 18 weeks.

FIG. 1. The level of AF-16 in affinity purified egg yolk as tested by ELISA using aP8. Samples from pooled (n=4) egg yolks were analysed and the net absorbance were determined.

Figure 2:
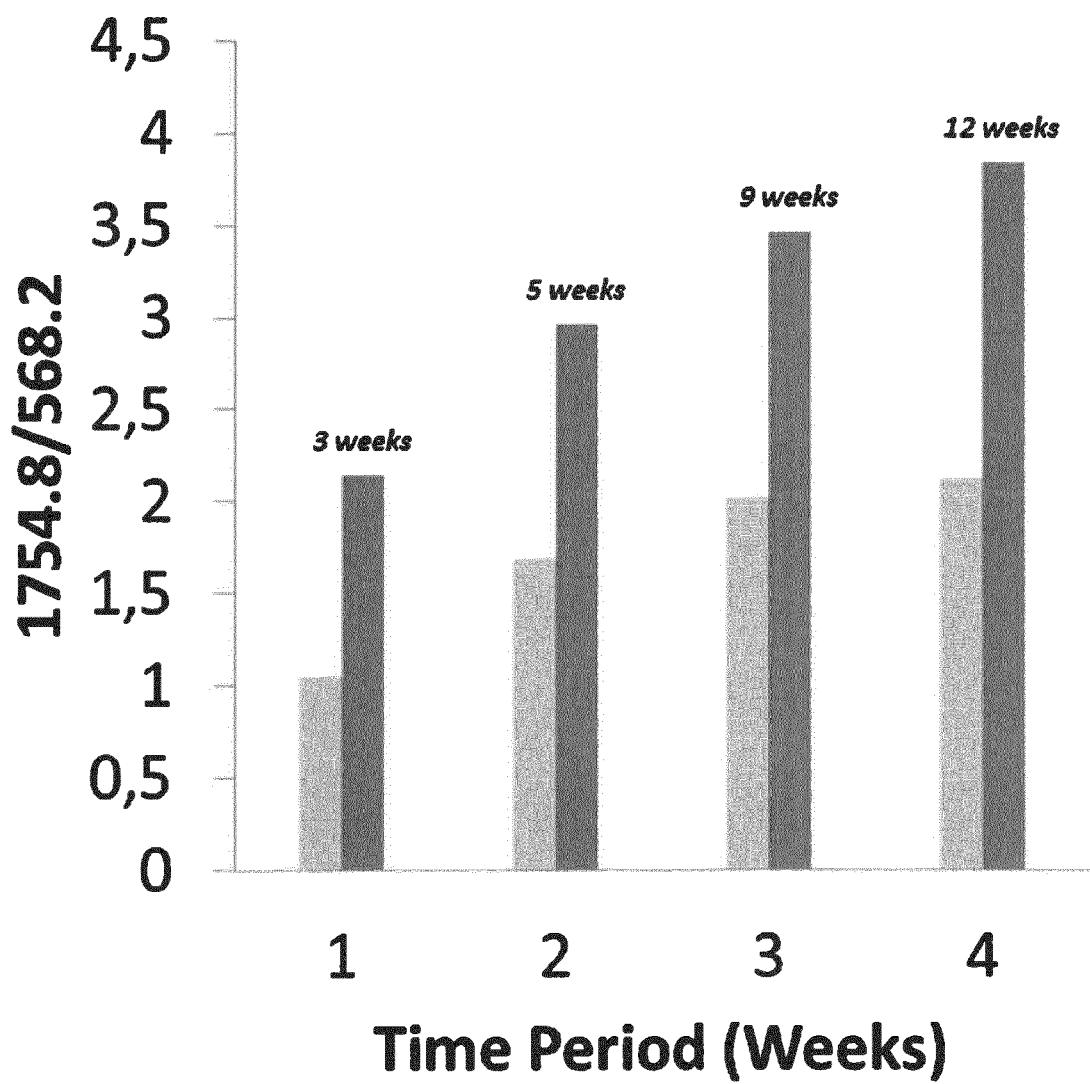
FIG. 2 displays the results of 30000 (light gray) and 10000 (dark gray) satisfactory laser shots collected from each sample showing the average normalized signal intensity of the AF-16 peptide from purified egg yolk samples ranging from 3-12 week.

Relative Quantification of AF-16 peptide in affinity purified egg yolk Samples was performed with MALDI-MS as can be seen in FIG. 2. The two different acquisition methods (30000 and 10000 satisfactory shots collected from each sample) rendered similar results and showed an increasing normalized signal intensity from 3 to 5 weeks, 5 to 9 weeks and 9 to 12 weeks respectively. Since HCCA was used as the matrix solution the signal intensities of AF-16 were normalized to the matrix signal 568.2 (3HCCA+H). Approximately two times increase in AF-16 signals observed in the samples from 3 to 12 weeks.

FIG. 2. 30000 (red) and 10000 (blue) satisfactory laser shots collected from each sample showing the average normalized signal intensity of the AF-16 peptide from purified egg yolk samples ranging from 3-12 weeks.

To evaluate the relative amount of the AF-16 peptide in egg yolk a dilution series of AF-16 peptide was added to affinity chromatography purified egg yolk samples and analyzed with MALDI. Results can be seen in FIG. 3. Results were normalized to 3 different internal mass peaks and we observed that normalizing to three different matrix signals gave similar results.

Figure 3:
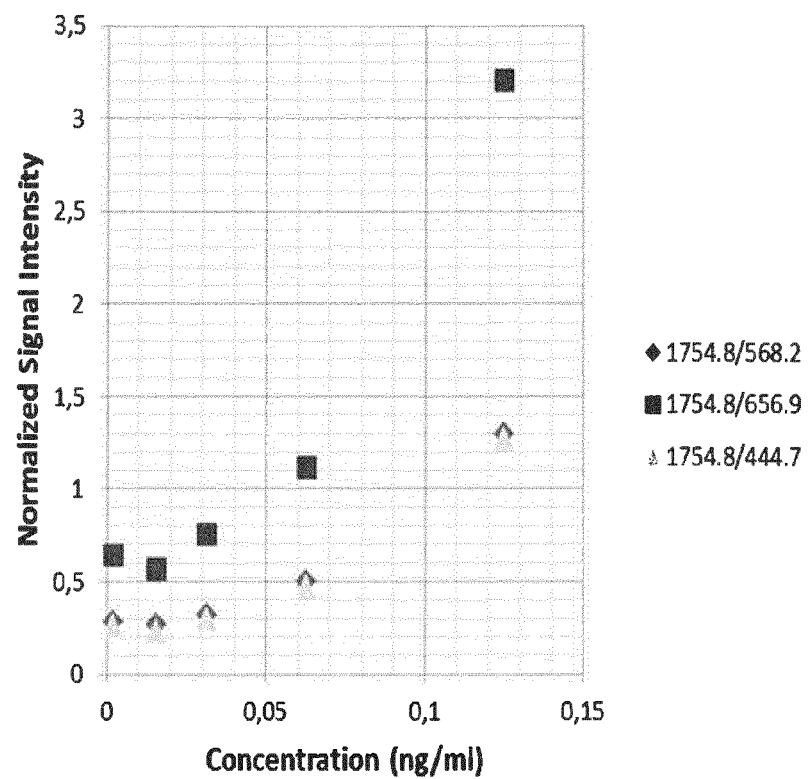
FIG. 3 shows the relative amount of the AF-16 peptide in egg yolk as analyzed with MALDI.
Figure 3:
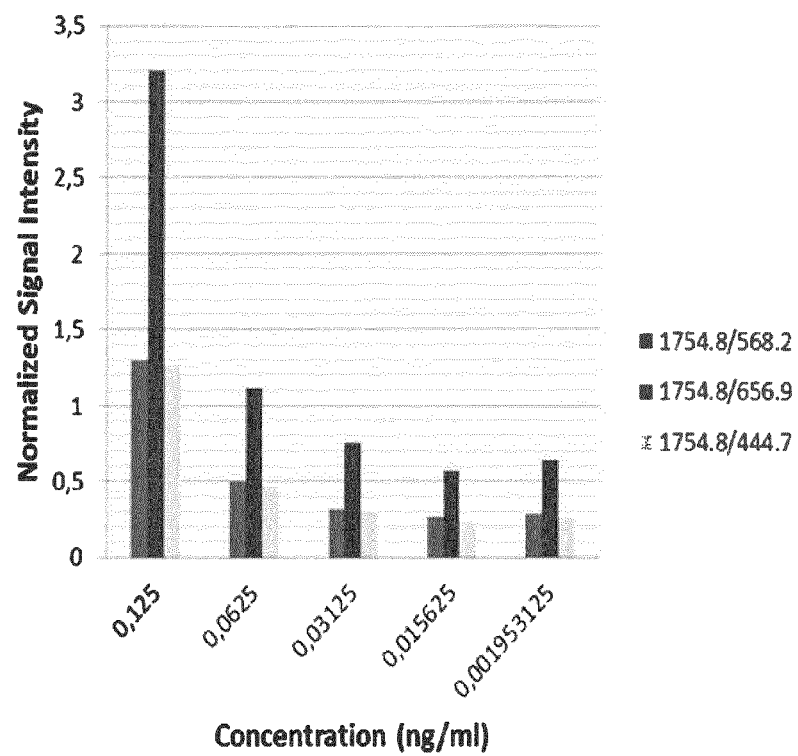

FIG. 3. Relative amount of the AF-16 peptide in egg yolk as analyzed with MALDI. Results were normalized to 3 different internal mass peaks Based on the normalized signal intensity in the dilution series we could estimate the relative amount of AF-16 peptide in the egg yolk samples to be in the range of 0.05 ng/ml after 12 weeks.

Based on the normalized signal intensity in the dilution series we could estimate the relative amount of Af-16 peptide in the egg yolk samples to be in the range of 0.05 ng/ml after 12 weeks.

Experiment 2

Antisecretory Factor Stops Diarrhea within Less Than Three Hours, without Side Effects.

Antisecretory Factor (AF) is part of the innate host defense system in man and animals. AF acts in conjunction with proteasomes and proteasome-complement C3 complexes, preventing hypersecretion and inflammation without side effects.

AF can be provided perorally as an egg-yolk powder, Salovum©.

In Pakistani children, suffering from acute diarrhea Salovum© treatment was previously shown to reduce the number of stools and improved their consistency within 10 hours vs. 18 hours for the placebo group.

A new batch of Salovum© (New Salovum) with a $10^2/10^3$-fold stronger antisecretory effect than the previous preparation was produced trying to accomplish an even more effective diarrhea treatment. This batch was used for treatment of children suffering from watery diarrhea and moderate to severe dehydration, selected at the Outpatients Paediatric Clinic, Childrens' Hospital, Lahore, Pakistan. Eight patients received one sachet of (New Salovum) (4 grams, group 1) while another eight received two sachets (New Salovum) (8 grams, group 2).

The protocol for diarrhea management remained uniform for all of the patients except for the (New Salovum) dose. At inclusion, the mean number of stools since morning was similar in both groups with 15±4.6 in group 1 and 13±4.5 in group 2, p=0.429. After the (New Salovum) drink, group 1 registered mean of 4 stools during the following 3 hours (65% reduction, p<0.001), while mean of 2.7 stools were seen in group 2 (68% reduction, p<0.000). Stool consistency improved similarly in both groups from initially watery (8, i.e. 100%) to watery (2, i.e. 25%) or semi-solid (6, i.e. 75%). No patient in group 2 showed signs of dehydration after the (New Salovum) intake, while six (75%) in group 1 presented some signs and two (25%) severe signs.

A reduction in stool numbers and improved consistency was seen within 91 minutes after the (New Salovum) drinks in group 1 and after 68 min. in group 2 (p=0.3302). No side effects were noted.

Giving New Salovum soon after the onset of diarrhea in underprivileged areas might be provided by e.g. village nurses, preferably starting soon after the onset of disease. This would reduce the need of applying a more qualified health care. New Salovum treatment of childhood diarrhea might thus result in improvement of child health enhancing growth and development, achieved at low cost and without the risk of side effects.

Table 2. Dose-response of New Salovum treatment in children suffering from diarrhoeal disease. Group 1 received one sachets (4 grams) and group 2 two sachets (8 grams) at inclusion. The clinical response to New Salovum treatment is recorded at the end of the first 3 hours registration period with the changes recorded during this time.

TABLE 2

| Variables | Group1 | Group2 | p value |
|---|---|---|---|
| Mean age (months) ± SD | 14.4375 ± 8.898 | 16.5 ± 5.318 | 0.5816 |
| Frequency of Stools: | | | |
| Stools passed since morning (mean ± SD) | 15 ± 4.62* | 13 ± 4.50** | 0.4291 |
| Stools passed in 3 hrs (mean ± SD) | 4.75 ± 2.91* | 2.75 ± 2.18** | 0.1430 |
| Percentage reduction: | 64.47% ($p < 0.0001$) | 68.11% ($p < 0000$) | |
| Consistency at admission: | | | |
| Watery | 8/8 100% | 8/8 100% | |
| After treatment: | | | |
| watery | 2/8 (25%) | 2/8 (25%) | 0.0035 |
| Semi/Solid | 6/8 (75%) | 6/8 (75%) | |
| Dehydration, clinical signs at presentation | | | |
| Some | 4 (50%) | 2 (25%) | |
| Moderate | 1 (12.5%) | 5 (62.5%) | |
| Severe | 3 (37.5%) | 1 (12.5%) | |
| Dehydration, clinical signs after treatment | | | |
| None | 0 | 8 (100%) | |
| Some | 6 (75%) | 0 | |
| Moderate | 0 | 0 | |
| Severe | 2 (25%) | 0 | |
| Mean time taken to respond by reducing no of stools and improving in consistency: | 91 minutes | 68 minutes | 0.3302 |

Note:
The total duration of OPD treatment did not extend to more than 3 hours during which all those sent home reported absence of all symptoms.
T test and Chisq tests were performed for comparisons between means and proportions.
*Before and after comparisons of mean stool numbers in group 1 was significant ($p < 0.0001$)
**Before and after comparisons of mean stool numbers 2 was significant ($p < 0.0000$)

Experiment 3

Method for the Estimation of Natural Antisecretory Proteins in Eggs.

1.75 grams of dried egg yolk powder is dissolved in a 6.4 ml of phosphate buffer solution (PBS), representing 20% of the dry matter of an egg yolk. 4 ml of this solution is added to 6 ml of PBS. (50% of the original NASP content.) The diluted sample is centrifuged at 2000 g for ten minutes; the supernatant is transferred to an agarose (Sepharose) column. The absorbed NASP is eluted with alpha-methyl glucoside and the 1 ml eluate containing the NASP is collected and dialyzed. (Yield 100%) The present patent application states:

The sample prepared as above is, prior to testing in the rat intestine model, diluted 500 or 1000 times. A 1 ml aliqoute of the diluted sample is injected intravenously prior to challenge the intestine with cholera toxin. The number of FIL-units is calculated from the intestine weight per centimeter in test and control groups of rats.

The content of NASP in eggs equals the result, as determined above and is multiplied by the inverse dilution rate.

Thus the analyzed content of NASP in the samples equals the result times multiplied by 1000 or 2000.

The invention claimed is:

1. An isolated and spray-dried, spray-dried egg yolk comprising at least 15 ng/g antisecretory factor (AF) protein fragment with the amino acid sequence of SEQ.ID.NO.1 measured by EIA in affinity purified egg yolk.

2. The egg yolk according to claim 1, wherein the egg is a poultry egg.

3. A food, feed and/or food-supplement comprising egg yolk according to claim 1.

4. A food according to claim 3 selected from the group consisting of pancake, omelet, ice cream, soft-drinks, yoghurt, bread, biscuits, pasta, grains, flakes, porridge, gruel, beverage compositions with or without electrolytes, a food preparation containing meat and meat products, fat and fat products, milk and milk products and foodbars.

5. An AF-16 and/or AF-8 inducing feed for poultry according to claim 3 comprising at least 1-2 grams tryptophan/kg feed and wherein said feed is provided in a pelleted form.

6. The AF-16-16 and/or AF-8 inducing feed for poultry according to claim 5, wherein said feed further comprises amino acids, sugars and amides in amounts and proportions such that the formation of AF-16 is stimulated in the poultry after consumption of said feed.

7. The AF-16-16 and/or AF-8 inducing feed for poultry according to claim 5, wherein said feed further comprises malted cereals in amounts and proportions such that the formation of AF-16 and/or AF-8 is stimulated in the poultry.

8. A pharmaceutical composition comprising egg yolk according to claim 1 and a suitable pharmaceutical carrier.

9. A pharmaceutical composition comprising egg yolk according to claim 8, wherein the suitable pharmaceutical carrier is selected from the group consisting of water, and PBS.

10. A pharmaceutical composition comprising egg yolk according to claim 8, which is further characterized by inducing at least 0.5 AF-Units in a patient in need thereof.

11. A process for producing an egg yolk according to claim 1, comprising at least 0.05 ng/ml antisecretory factor (AF) protein fragment with an amino acid sequence as disclosed in SEQ.ID.NO.1 and/or in SEQ.ID.NO.2, said method comprising
   a. for at least 4 weeks feeding poultry an AF-16 and/or AF-8 inducing feed for poultry according to claim 5 and thereafter
   b. harvesting at least one egg comprising egg yolk and egg white from said poultry,
   c. separating egg yolk from egg white, and
   d. freeze drying, fluid bed drying, grinding, leaching, extracting, evaporating, membrane filtering, and/or drying said egg yolk.

12. A process for producing an egg yolk according to claim 11, wherein said poultry is a gallinaceous bird.

13. Egg yolk produced according to claim 11.

14. Egg yolk according to claim 13, wherein said egg yolk comprises at least 0.05 ng/ml antisecretory factor (AF) protein fragment with an amino acid sequence as disclosed in SEQ.ID.NO.1 and/or SEQ.ID.NO.2.

15. A process for producing an egg yolk according to claim 1, comprising at least 0.05 ng/ml antisecretory factor (AF) protein fragment with the amino acid sequence of SEQ.ID.NO.1 and/or in SEQ.ID.NO.2, said method comprising
   a. for at least 12 weeks feeding poultry an AF-16 and/or AF-8 inducing feed for poultry according to claim 5 and thereafter
   b. harvesting at least one egg comprising egg yolk and egg white from said poultry,
   c. separating egg yolk from egg white, and
   d. freeze-drying, fluid bed drying, grinding, leaching, extracting, evaporating, membrane-filtering, and/or drying said egg yolk.

16. A method for treating and/or preventing disease-like conditions caused by extreme body fluid discharge, discomfort due to physiological unbalance, inflammations, edema, arthritis, glaucoma, migraine, burns and/or traumatic injuries in and on the body, for use in treating diarrhea and/or dehydration, for use in treating and/or preventing any one of the diseases selected from the group consisting of inflammatory diseases, cancer, glioblastoma, intraocular hypertension, compartment syndrome, Parkinson's Disease, Alzheimer's Disease and diabetes, said method comprising administering a pharmaceutically effective amount of egg yolk according to claim 1 to a subject in need thereof.

17. A method for neuroprotection, optimizing delivery and/or cellular uptake of a pharmaceutical substance and/or formulation, such as an anticancer drug, immune therapy, radiation therapy or a gene delivery into a tumor cell, improving the repair of nervous tissue, improving proliferation of stem and progenitor cells, improving apoptosis stem and progenitor cells, improving differentiation stem and progenitor cells, improving migration of stem and progenitor cells and cells derived thereof and for the treatment of conditions associated with loss and/or gain of neuronal cells, said method comprising administering a pharmaceutically effective amount of egg yolk according to claim 1 to a subject in need thereof.

18. The method of claim 16, wherein administration of the egg yolk induces at least 0.5 AF-Units in the subject between 60-120 min after administration.

* * * * *